United States Patent [19]
Braatz et al.

[11] Patent Number: 5,617,906
[45] Date of Patent: Apr. 8, 1997

[54] CONTAINER FOR ANAESTHETIC AGENT

[75] Inventors: Robert E. Braatz, Sun Prairie, Wis.; Raymond S. Gregory, Bingley, Great Britain; Robert A. Heaton, Skipton, Great Britain; Keith Whitaker, Keighley, Great Britain; David C. Sampson, Cowling, Great Britain

[73] Assignee: The BOC Group plc, Windlesham, England

[21] Appl. No.: 451,352

[22] Filed: May 26, 1995

Related U.S. Application Data

[63] Continuation of Ser. No. 90,082, filed as PCT/GB92/00139 Jan. 24, 1992 published as WO92/12752 Aug. 6, 1992, abandoned.

[30] Foreign Application Priority Data

Jan. 24, 1991 [GB] United Kingdom .................. 9101560

[51] Int. Cl.⁶ .............................. B65B 1/04; B65B 3/04
[52] U.S. Cl. .............................. 141/21; 141/59; 141/292; 141/364; 141/352
[58] Field of Search ............................. 141/21, 198, 285, 141/286, 290–293, 351, 352, 363–366, 346, 348, 349, 354, 357, 59; 215/231; 128/200.14, 200.16, 200.21; 222/110

[56] References Cited

U.S. PATENT DOCUMENTS

| | | | |
|---|---|---|---|
| 2,112,199 | 3/1938 | Kantor et al. | 141/287 |
| 2,197,588 | 4/1940 | Namur | 141/294 |
| 2,685,396 | 8/1954 | Day et al. | 141/293 |
| 3,125,135 | 3/1964 | Boyer et al. | 141/293 |
| 3,133,565 | 5/1964 | Ikeda | 141/293 |
| 3,289,712 | 12/1966 | Smith | 141/352 |
| 3,540,402 | 11/1970 | Kocher | 141/292 |
| 3,606,096 | 9/1971 | Campbell | 141/292 |
| 4,667,710 | 5/1987 | Wu | 141/292 |
| 4,982,881 | 1/1991 | Amrein | 141/351 |

FOREIGN PATENT DOCUMENTS

| | | |
|---|---|---|
| 0242979 | 10/1987 | European Pat. Off. . |
| 0295671 | 6/1988 | European Pat. Off. . |
| 0467068 | 1/1992 | European Pat. Off. . |
| 8429005 | 2/1985 | Germany . |
| 9015951 | 12/1990 | WIPO . |

*Primary Examiner*—Henry J. Recla
*Assistant Examiner*—Steven O. Douglas
*Attorney, Agent, or Firm*—Roger M. Rathbun; R. Hain Swope

[57] ABSTRACT

A container (2) for a liquid anaesthetic agent for supplying the agent to an anaesthetic vaporiser comprises a reservoir for the liquid agent, a valve (6) which, when closed, prevents the flow of the liquid agent from the reservoir, a tubular outlet (10) through which the liquid can leave the reservoir when the valve is open. An O-ring (20) at the free end of the conduit provides a sealing surface for forming a seal with a corresponding sealing surface provided at an inlet to a vaporiser to which the anaesthetic agent is to be supplied. A flange (22) engages a guide on the vaporiser, to retain the container in contact with the vaporiser.

15 Claims, 5 Drawing Sheets

CONTAINER FOR ANAESTHETIC AGENT

This is a continuation of application Ser. No. 08/090,082, filed as PCT/GB92/00139 Jan. 24, 1992 published as WO92/12752 Aug. 6, 1992, now abandoned.

This invention relates to a container for a liquid anaesthetic agent, for supplying the agent to a sump of an anaesthetic vaporiser, and to techniques for refilling the sump using the container.

An anaesthetic agent is administered to a patient during anaesthesia by means of an anaesthetic vaporiser. The agent is supplied to the patient from a sump within the vaporiser as a vapour, the agent being stored in the sump as a liquid.

Systems for filling the sump of an anaesthetic vaporiser with anaesthetic agent are disclosed in GB-1193241 and GB-1394216. These systems include a bottle in which the agent is supplied to the operator of the vaporiser, and a flexible conduit which can be mounted on the bottle opening by the operator, through which the agent passes from the bottle into the vaporiser.

Known filling systems have the disadvantage that anaesthetic agent can escape from the bottle after the bottle has been opened and before the conduit is positioned on the bottle opening. This disadvantage is becoming of increasing significance as attention is given to the conditions to which medical workers are exposed during their work.

The present invention provides a container for a liquid anaesthetic agent which includes means for preventing loss of anaesthetic agent from the container.

In one aspect, the invention provides a container for supplying a liquid anaesthetic agent to an anaesthetic vaporiser, the container comprising:

(a) a reservoir which contains a quantity of a liquid anaesthetic agent;

(b) a valve which, when closed, prevents the flow of the liquid agent from the reservoir;

(c) a tubular outlet through which the liquid can leave the reservoir when the valve is open; and (d) a sealing surface provided towards the free end of the outlet extending around the perimeter thereof, for forming a seal with a corresponding sealing surface provided at an inlet to a vaporiser to which the anaesthetic agent is to be supplied.

The present invention has the advantage that it makes it possible for anaesthetic agent to be sealed in a container under controlled conditions, generally at a location remote from that at which the agent is to be administered to a patient, for example at the site at which the agent is manufactured. The agent is then able to remain in the container, and need not be exposed to atmosphere, at any time prior to administration to a patient. This allows the particular problem of the effect of anaesthetic agents on operators of anaesthetic vaporiser equipment, and on other medical workers, arising from escaping agent at the time of supply of the agent to a vaporiser to be solved.

The container of the present invention finds application in the supply of anaesthetic agents such as 2-chloro-1,1,2-trifluoromethyl difluoromethyl ether (sold under the trade marks Enflurane and Ethrane), 1-bromo-1-chloro-2,2,2-trifluoroethane (Halothane and Fluothane), 1-chloro-2,2,2-trifluoroethyl difluoromethyl ether (Isoflurane and Forane) and fluoromethyl 2,2,2-trifluoro-1-(trifluoromethyl)ethyl ether (Sevoflurane). The technique of the invention is particularly well suited to the supply of volatile anaesthetic agents, for example agents having a boiling points not more than about 5° C. above ambient temperature. An example of an agent which can be volatile under certain conditions is 2-(difluoromethoxy)-1,1,1,2-tetrafluoroethane (sold under the trade marks Desflurane and Suprane). The problem of an anaesthetic agent escaping from a container while it is being supplied to a vaporiser is particularly severe in the case of a volatile agent since, under relatively high temperature conditions (that is at temperatures around or above the boiling point of the agent), the agent within the reservoir in the container can be at elevated pressure. Furthermore, anaesthetic agent contained within the sump of a vaporiser can be at elevated pressure, for similar reasons. The refilling technique made possible by the container of the present invention allows an anaesthetic agent at elevated pressure within a container to be supplied to the sump of an anaesthetic vaporiser, containing the agent also at elevated pressure, and to do so without leakage of the agent.

Preferably, the container includes means for forming a connection between the container and a vaporiser to retain the container on the vaporiser. This can allow the seal between the container and the vaporiser to withstand pressure within either or both of them, to which the seal is exposed when fluid is able to pass between them.

Preferably, the means for connecting the container to the vaporiser comprises a formation which presents a surface facing in a direction substantially opposite to the direction in which fluid passes out of the reservoir through the outlet. The surface may be provided by, for example, a flange, or one or more recesses. Preferably, the surface extends around the entire perimeter of the container, so that the connection means is able to function irrespective of the rotational orientation of the container.

The outlet may be arranged to receive a conduit, for example one which is mounted on an anaesthetic vaporiser, through which the anaesthetic agent can flow from the reservoir to the sump in the vaporiser. In many circumstances, however, it is preferred that the outlet includes a conduit which extends from the reservoir, to engage, for example to be received in, an inlet on a vaporiser to provide a channel through which fluid flows from the reservoir into the sump of a vaporiser. This arrangement has the advantage that the conduit does not remain on the vaporiser, where it might be liable to physical damage.

It is generally preferred that a conduit provided as part of the container is rigid so that it can withstand compression loads longitudinally, for example that it be made from a relatively undeformable material.

The sealing surface on the conduit will be provided of a material and with a suitable configuration to form a seal to the corresponding sealing surface on an inlet to an anaesthetic vaporiser. Examples of suitable sealing arrangements include ones provided by a deformable O-ring which engages a surface, for example a surface of a cylindrical body, which may be an external or internal (in which case the body will be tubular) surface.

Preferably, the valve comprises a plate member and an aperture against which the plate member is forced to close the aperture against fluid flow through it, the plate member being forced away from the aperture when a seal is made between the container and a sump of a vaporiser.

The container may include an insert extending from the plate member, through which force can be applied to the plate member to urge it away from the aperture to open the valve. The insert and the plate member may be provided as an integral part, for example as a result of a moulding operation. The insert may define a plurality of chambers in the tubular outlet, for flow of liquid anaesthetic agent from the reservoir, and for return flow of anaesthetic agent vapour into the reservoir, respectively. The chambers may be coaxial. In another arrangement, the chambers may be defined by one or more partitions which extend across the tube of the outlet, for example by means of two partitions which extend across the conduit approximately perpendicularly to one another to define four chambers.

The valve and the outlet, with an outlet conduit if present, may be attached to the reservoir by a technique which seals the attachment to prevent interference therewith. For example, they may be attached by crimping, or by means of a screw threaded connection which might be sealed for example by means of a plastic film which is caused to shrink onto the connection by the application thereto of heat. The use of a permanent attachment technique has the advantage that it is possible to detect interference with the seal to the reservoir, which might be associated with for example contamination of the anaesthetic agent contained within it.

The anaesthetic vaporiser to which anaesthetic agent might be supplied from the container of the present invention will generally have at least one valve which, when closed, prevents passage of fluid into and out of the sump. It will be preferred at least for the sump to have a valve associated with the inlet, which engages the outlet from the container when the a seal between the two is formed. That valve may comprise a plate member and an aperture against which the plate member is forced to close the aperture against fluid flow through it, the plate member being forced away from the aperture when a seal is made between the container and the sump. This valve, like the valve on the container, may be opened by means of an insert extending from the plate member, through which force can be applied to the plate member to urge it away from the aperture to open the valve. When there are plate members in the valves on the container and the sump, and both of the plate members are to be moved by means of an insert, they may be moved by a single insert, or by a pair of inserts, each associated with a respective one of the plate members, which act against one another to cause the plate members to move and to open the valves.

Details of an anaesthetic vaporiser, and of filling systems which comprise an anaesthetic vaporiser and a supply container for an anaesthetic agent, are disclosed in WO-A-92/12753 entitled Fluid Delivery Systems, filed with the present application and claiming priority from UK patent application number 9101560.2. All subject matter disclosed in that document is incorporated in the specification of the present application by this reference to the document.

Embodiments of the present invention will now be described, by way of example, with reference to the accompanying drawings, in which.

Figure 1:
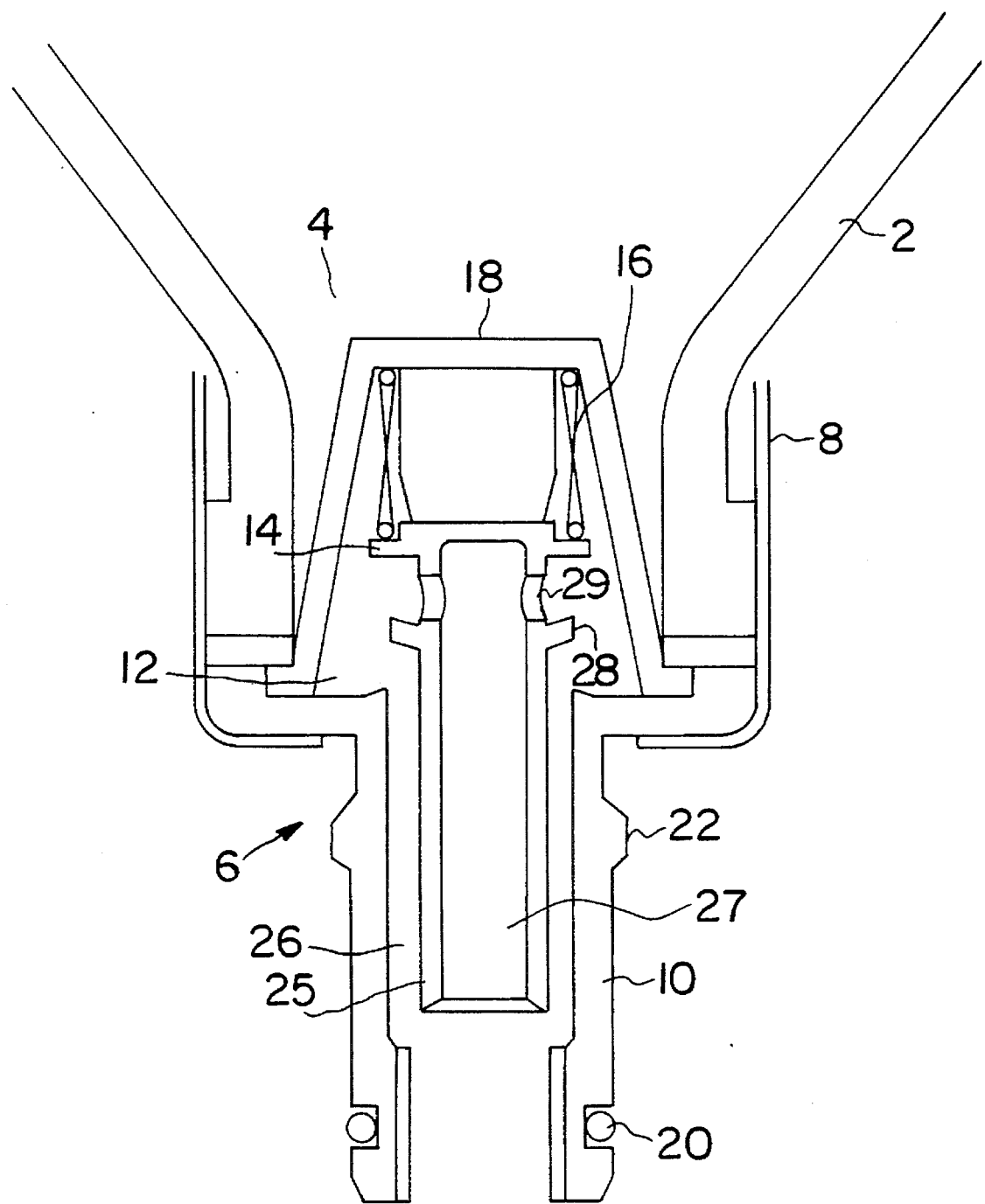
FIG. 1 is a schematic cross-section a part of a container for an anaesthetic agent, showing the outlet from that container.

Referring to the drawings, FIG. 1 shows a container 2 for an anaesthetic agent, in the form of a bottle which provides a reservoir within it for anaesthetic agent. The container is formed from glass, which is provided with a coating of plastic film, which has the advantage that pieces of the material of the bottle which arise from fracture, for example under pressure from the anaesthetic vapour when the bottle is exposed to elevated temperature, are retained loosely connected to one another. The outlet 4 from the reservoir is closed by means of a valve assembly 6, which is attached to the outlet from the reservoir in the container by means of a crimped ferrule. The outlet is provided by a conduit 10, through which fluid is supplied from the reservoir in the container 2. The aperture 12 into the conduit 10 at the end proximal to the reservoir is closed by means of a moveable valve member 14. The valve member can move between a closed position in which it closes the aperture 12 and an open position as shown in FIG. 1. A spring 16 acts to force the valve member 14 towards the closed position. A cage 18 restricts movement of the valve member 14 in the open position.

A screw cap may be provided to close the bottle, to provide a seal against egress of anaesthetic agent, liquid or vapour, during transportation of the bottle. The cap may be provided with a deformable seal within it, by which a seal can be made to the bottle.

At the end remote from the container 2, the conduit 10 has an O-ring 20 provided in a groove.

The conduit 10 has formed on its outer surface, towards the end proximal to the reservoir, a circumferentially extending flange 22, which presents a surface facing in a direction substantially opposite to the direction in which fluid passes out of the reservoir through the outlet.

Attached to the valve member 14 is a cylindrical partition 25 which extends through the conduit 10, coaxially with it. The partition defines two coaxial chambers 26, 27 within the conduit. The outer chamber 26 is for flow of fluid, generally liquid, from the reservoir in the container 2 into the sump of a vaporiser, and the inner chamber 27 is for flow of fluid, which may be liquid or vapour, in the return direction. A deflector 28 can be provided towards the end of the partition adjacent to the valve member, to divide the flows of fluid in the two chambers, and ports 29 are provided through which fluid can pass out of the inner chamber 27.

Figure 2:
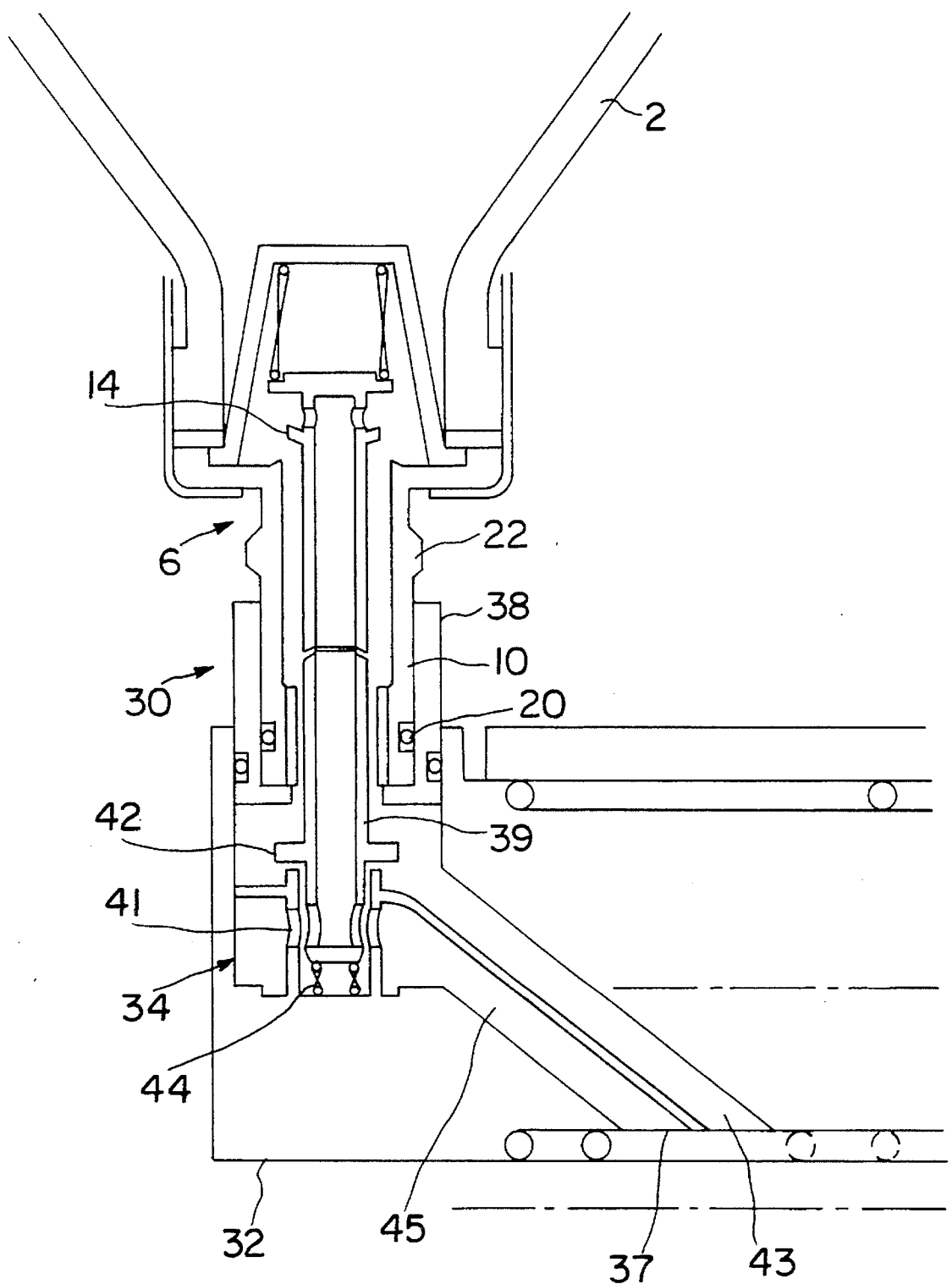
FIG. 2 is a schematic cross-section through the container shown in FIG. 1 connected to the inlet of a sump.

FIG. 2 shows the container 2 and valve assembly 6 depicted in FIG. 1 mounted on the inlet 30 of a sump contained within an anaesthetic vaporiser 32. The inlet 30 has a valve 34 provided within it, which includes a valve member 42 which, when closed, abuts the lower end (as shown) of the inlet conduit 10. In this position, the valve is closed and prevents flow of fluid between the inlet conduit and the sump. As shown in FIG. 2, the valve member is displaced from the end of the conduit 10, against the force exerted by the fluid within the sump and force exerted by a spring 44. The inlet 30 also includes a cylindrical receptacle 38 for the conduit 10 on the container valve assembly, and a cylindrical partition 39 which extends through the receptacle, coaxially with it. The partition defines two coaxial chambers within the receptacle, which communicate with the chambers 26, 27 defined by the partition 25 within the nozzle 10. The inner chamber terminates at ports 41 through which fluid can enter and leave that chamber.

Two passageways 43, 45 communicating with respective ones of the ports 41 from the coaxial chambers within the receptacle, allow flow of fluid between the sump within the vaporiser. The first passageway 43 provides for flow of fluid, generally liquid, from the supply container into the sump, and the second passageway 45 provides for flow of fluid in the return direction.

Figure 3:
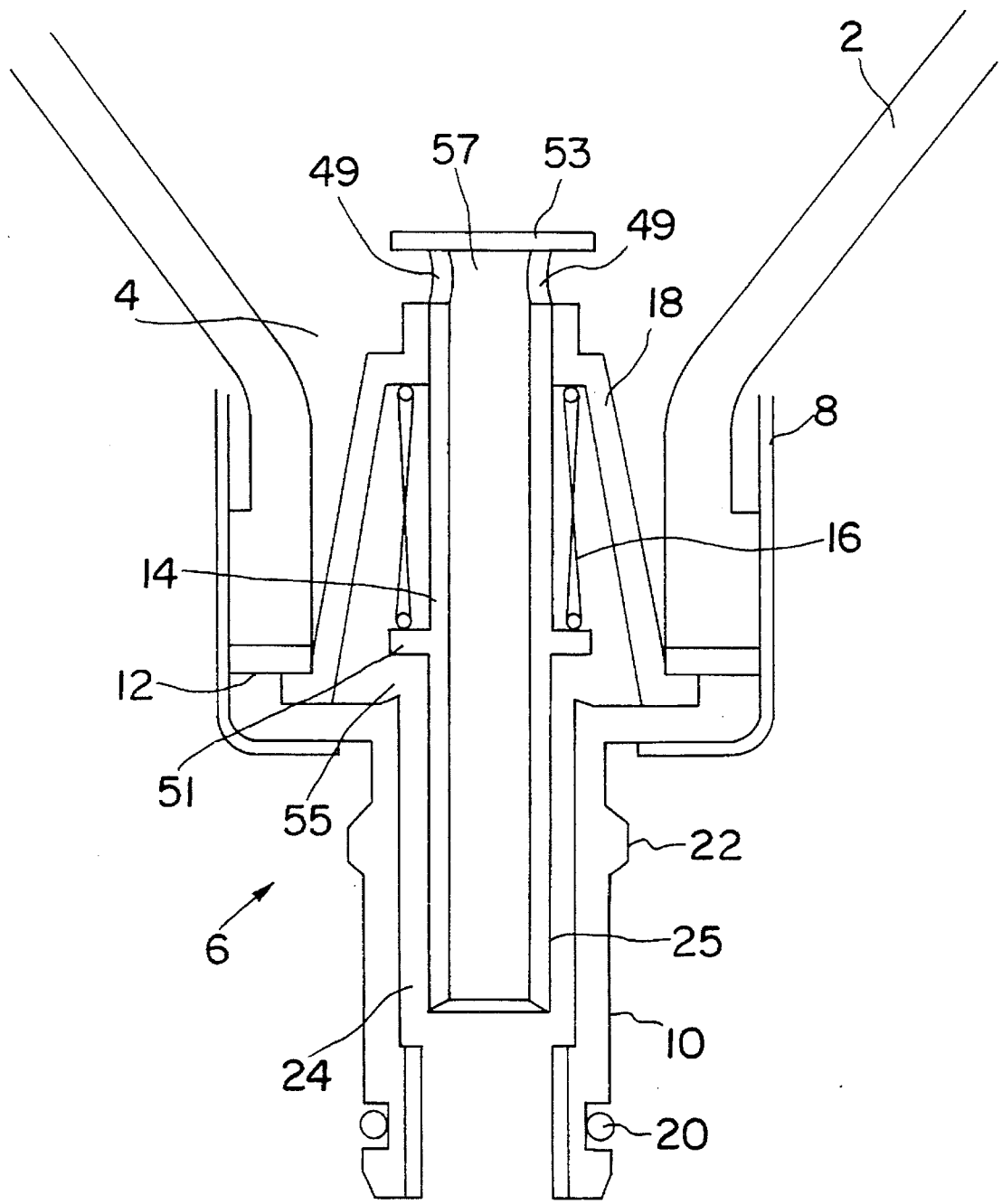
FIG. 3 is a schematic cross-section through another embodiment of outlet from a container for an anaesthetic agent.

FIG. 3 shows a container 2 for an anaesthetic agent, with an outlet 4 which is closed by means of a valve assembly 6.

The valve assembly includes a conduit 10 which is closed by means of a moveable valve member 14. The conduit contains a cylindrical partition 25 which divides the conduit into two coaxial passageways. Access of fluid to the inner passageway is gained via ports 49.

The valve member 14 can move between a closed position in which flanges 51, 53 close openings 55, 57 into the passageways in the conduit 10, and an open position as shown in FIG. 3. A spring 16 acts to force the valve member 14 towards the closed position, and a cage 18 restricts movement of the valve member 14 in the open position.

Figure 4A:
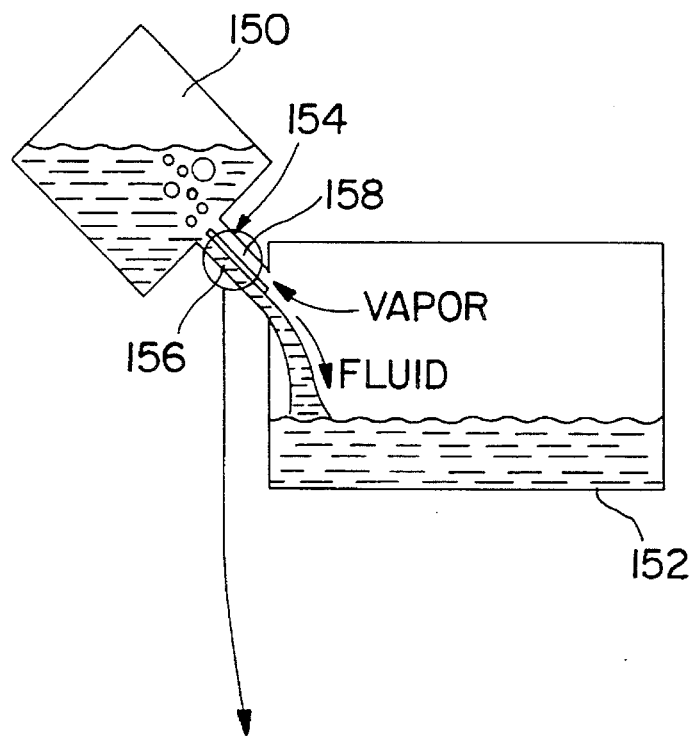
FIGS. 4A–4C are an isometric view of an embodiment of conduit through which liquid can be supplied from the outlet from the reservoir of the container to a sump.

FIG. 4a shows schematically a container 150 for an anaesthetic agent and sump within an anaesthetic vaporiser 152, with a conduit 154 connecting them. The conduit is divided into two or more chambers, at least one of the chambers being located above at least one other of the chambers. The conduit extends from the vaporiser towards the supply container at an angle of about 45° to the vertical. The lower chamber 156 of the conduit contains liquid passing from the supply container 150 to the vaporiser 152. The upper conduit 158 provides a path for flow of vapour from the sump to the supply container. This makes it possible for vapour pressure between the two containers 150, 152 to be equalised, and facilitates flow of liquid from the supply container to the sump.

Figures 4B, 4C:
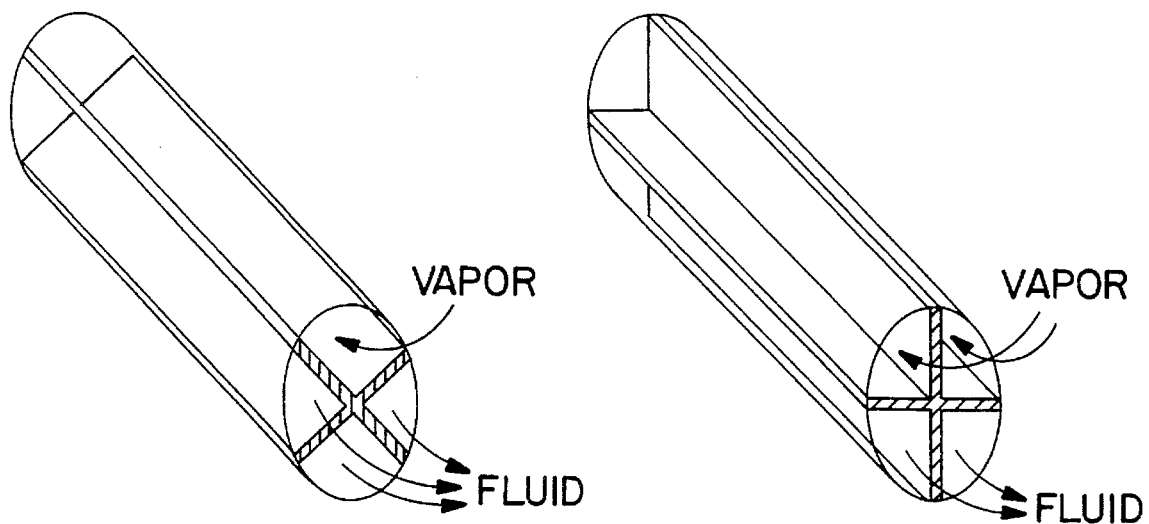

FIGS. 4b and 4c show a preferred conduit in different orientations. Each conduit has a circular cross section, and contains an insert made up of two partitions arranged substantially perpendicularly to one another. The two partitions divide the container into four chambers. Whatever the orientation of the conduit, at least one of the chambers will be located above at least one of the other chambers within the conduit, thus providing respective pathways for flow of liquid and flow of vapour.

Figure 5A:
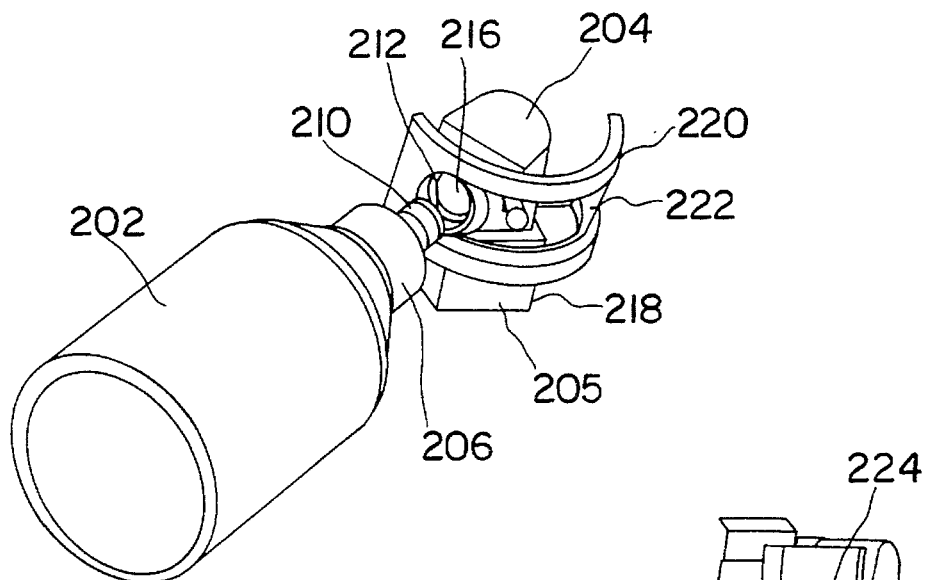
FIGS. 5A–5C show views of a bottle for an anaesthetic agent, and an anaesthetic vaporiser to which the bottle can be connected.
Figure 5B:
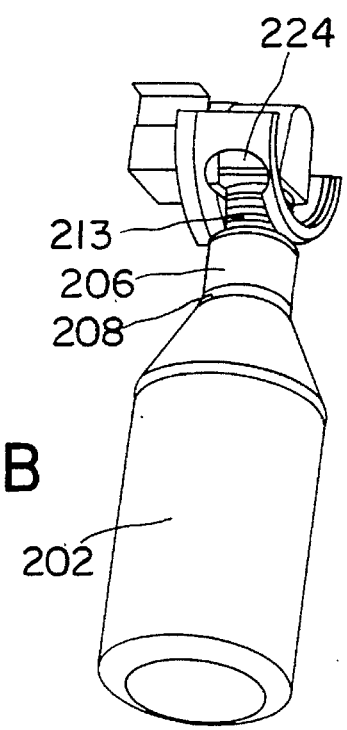
Figure 5C:
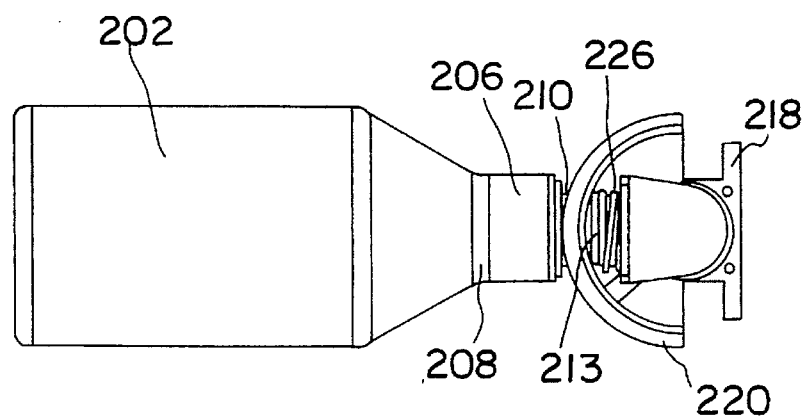

FIGS. 5a to 5c show views of a container 202 for an anaesthetic agent under pressure, which is mounted on an inlet 204 to a sump in an anaesthetic vaporiser 205, for supply of the agent from a reservoir in the container into the sump.

The reservoir in the container 202 includes a valve assembly 206 which is clamped onto the mouth of the reservoir by means of a ferrule 208, generally as described with reference to FIG. 1 above. The valve assembly includes a valve member which, when the reservoir is not connected to the sump, prevents escape of the agent from the reservoir. It also includes a conduit 210 by which flow of the agent from the reservoir is directed. An O-ring 212 and an outwardly extending flange 213 are provided on the outer surface of the conduit towards its free end.

The vaporiser 205 includes a inlet 214 for the free end of the conduit 210 on the reservoir. A valve, with an insert for opening that valve and the valve on the reservoir, may be provided for example similar to those components of the vaporiser described with reference to FIG. 2. The inlet includes a receptacle 216 which contains a sealing surface on its internal surface against which the O-ring 212 acts to form a seal between the reservoir in the container and the vaporiser. The inlet is mounted for rotation on the housing 218 of the vaporiser (in which the pump is located), and contains a conduit through which anaesthetic agent entering the vaporiser from a container through the inlet passes into the sump. The conduit has at the end proximal to the housing an opening in its side wall which, together with an opening into the sump, provide a valve by which flow of fluid into the sump can be controlled. As a result, rotation of the inlet about the axis will cause the valve provided by the openings in the conduit and the sump to open.

The housing 218 has a guide 220 mounted on it for the rotation of the inlet 204. The guide has a key-hole shaped slot 222 provided in it, including a widened portion 224 at one end. The widened portion is able to receive the receptacle 216 in it, the receptacle being urged outwardly from the body of the inlet into the widened portion of the slot by means of a spring 226. The inlet is prevented from rotating relative to the housing of the vaporiser while the receptacle is so engaged in the widened portion of the slot as a result of the side walls of the slot engaging the sides of the receptacle.

The receptacle 216 can be caused to move against the force exerted by the spring 226 by insertion of the free end of the conduit 210, so as to free the receptacle for movement along the slot 222 as the inlet is rotated relative to the vaporiser housing. As the inlet 204 and the reservoir in the container 202, whose conduit has been inserted into the inlet, are rotated relative to the slot, the side walls of the slot 222 engage the flange provided on the free end of the conduit, and retain the container engaged with the receptacle. This prevents the container from being forced away from the receptacle when connection between them is exposed to elevated pressure within the reservoir in the container and the sump.

The axis about which the inlet rotates relative to the housing is preferably horizontal. It is particularly preferred that the axis is arranged so that the inlet is moved upwardly to open the valve into the sump. Preferably, a reservoir engaging the inlet requires to be held in the raised (valve open) position for the valve to remain open, so that the valve is only open while an operator is present. If necessary, the receptacle may be biassed towards the downward facing position, for example by means of a spring which acts between the inlet and the housing.

We claim:

1. An anaesthetic agent container for supplying a liquid anaesthetic agent to an anaesthetic vaporizer, the container comprising:

(a) a reservoir containing a quantity of a volatile liquid anaesthetic agent;

(b) a valve which, when closed, closes said reservoir and prevents the flow of said volatile liquid anesthetic agent and vapor agent from the reservoir;

(c) a tubular outlet having one passageway through which said volatile liquid anesthetic agent can leave the reservoir and a second, separate passageway in said tubular outlet through which vapor can enter the reservoir when the valve is open;

(d) a sealing surface provided towards the free end of the outlet extending around the perimeter thereof for forming a seal with a corresponding sealing surface provided at an inlet to a vaporizer to which said anaesthetic agent is to be supplied; and (e) a formation formed on the outer surface of the tubular outlet which presents a surface facing in a direction substantially opposite to the direction in which agent passes out of the reservoir through the outlet for latching with a cooperating surface provided at the inlet to the vaporizer to which the anaesthetic agent is to be supplied.

2. A container as claimed in claim 1, in which the valve comprises a plate member and an aperture against which the plate member is forced to close the aperture against fluid flow through it, the plate member being forced away from the aperture when a seal is made between the container and the sump of a vaporiser to which anaesthetic agent is to be supplied.

3. A container as claimed in claim 2, which includes an insert extending from the plate member, through which force can be applied to the plate member to urge it away from the aperture to open the valve.

4. A container as claimed in claim 3, in which the insert defines a plurality of chambers in the tubular outlet, for flow of liquid anaesthetic agent from the reservoir, and for return flow of anaesthetic agent vapour into the reservoir, respectively.

5. A container is claimed in claim 4, in which the said chambers are coaxial.

6. A container as claimed in claim 1, in which the outlet comprises a conduit which extends from the reservoir and which is rigid.

7. A container as claimed in claim 6, in which the sealing surface is provided on an outer surface of the conduit.

8. A container as claimed in claim 7, in which the sealing surface is provided by a deformable O-ring.

9. A container as claimed in claim 1, in which there is included a cap which can be applied to the outlet from the reservoir to close the outlet.

10. An anaesthetic agent container for supplying a liquid anaesthetic agent to the sump of an anaesthetic vaporizer, the container comprising:

(a) a closed reservoir containing a quantity of a volatile liquid anaesthetic agent;

(b) a valve which, when closed, prevents the flow of said volatile liquid anaesthetic agent and vapor agent from said reservoir, said valve comprising a plate member and an aperture against which said plate member is forced to close said aperture against the flow of said volatile liquid anaesthetic and vapor agent therethrough, said plate member being spring-biased to the closed position and being movable to the open position by a member extending from the anaesthetic vaporizer;

(c) a tubular outlet through which said volatile liquid anaesthetic agent can leave the reservoir when the valve is open;

(d) a sealing surface on the tubular outlet located towards the free end of the outlet for forming a seal with a corresponding sealing surface provided at an inlet to a vaporizer; and (e) an insert within the tubular outlet and extending from the plate member, said insert defining a plurality of separate chambers in the tubular outlet for flow of said volatile liquid anaesthetic agent from said reservoir, and for return flow of anaesthetic agent vapour into said reservoir, respectively.

11. A container as claimed in claim 10, in which the said chambers are coaxial.

12. An anaesthetic agent container as defined in claim 10 wherein said sealing surface forms a pressure tight seal with the corresponding sealing surface provided at an inlet to a vaporizer.

13. An anaesthetic agent container as defined in claim 10 wherein said insert extends from said plate in the direction in which liquid agent passes out of the reservoir through said tubular outlet.

14. An anaesthetic agent container for supplying a liquid anaesthetic agent to an anaesthetic vaporizer, the container comprising:

(a) a closed reservoir containing a quantity of a volatile liquid anaesthetic agent;

(b) a valve which, when closed, prevents the flow of said volatile liquid anaesthetic agent and vapor agent from said reservoir;

(c) a tubular outlet through which said volatile liquid anaesthetic agent can leave said reservoir and vapor can enter said reservoir when said valve is open;

(d) a sealing surface provided towards the free end of said tubular outlet extending around the perimeter thereof for forming a seal with a corresponding sealing surface provided at an inlet to a vaporizer to which said volatile liquid anaesthetic agent is to be supplied; and (e) means for forming a connection between said container and a vaporizer to retain said container on the vaporizer, said means comprising a formation formed on the outer surface of said tubular outlet which presents a surface facing in a direction substantially opposite to the direction in which said volatile liquid anaesthetic agent passes out of said reservoir through said outlet for latching with a cooperating surface provided at the inlet to the vaporizer to which said volatile liquid anaesthetic agent is to be supplied.

15. An anaesthetic agent container as claimed in claim 14 in which the formation comprises a flange which extends at least partially around the perimeter of the container.

* * * * *